(12) United States Patent
Kaufmann et al.

(10) Patent No.: US 9,956,380 B2
(45) Date of Patent: May 1, 2018

(54) BLOOD CANNULA

(71) Applicant: enmodes GmbH, Aachen (DE)

(72) Inventors: Tim Kaufmann, Aachen (DE); Ulrich Steinseifer, Hauset (BE); Anton Moritz, Dreieich (DE)

(73) Assignee: ENMODES GMBH, Aachen (DE)

(*) Notice: Subject to any disclaimer, the term of this patent is extended or adjusted under 35 U.S.C. 154(b) by 278 days.

(21) Appl. No.: 14/762,142

(22) PCT Filed: Jan. 6, 2014

(86) PCT No.: PCT/EP2014/000004
§ 371 (c)(1),
(2) Date: Jul. 20, 2015

(87) PCT Pub. No.: WO2014/111239
PCT Pub. Date: Jul. 24, 2014

(65) Prior Publication Data
US 2015/0352322 A1 Dec. 10, 2015

(30) Foreign Application Priority Data
Jan. 21, 2013 (EP) .................................... 13000286

(51) Int. Cl.
*A61M 25/00* (2006.01)
(52) U.S. Cl.
CPC . *A61M 25/0068* (2013.01); *A61M 2025/0073* (2013.01); *A61M 2025/0081* (2013.01)

(58) Field of Classification Search
CPC .. A61M 2025/0073; A61M 2025/0081; A61M 25/0068
See application file for complete search history.

(56) References Cited

U.S. PATENT DOCUMENTS

| | | | | |
|---|---|---|---|---|
| 5,616,137 A | * | 4/1997 | Lindsay | A61M 25/007 604/264 |
| 6,706,033 B1 | * | 3/2004 | Martinez | A61B 17/3415 600/130 |
| 7,799,046 B2 | | 9/2010 | White | |

FOREIGN PATENT DOCUMENTS

| | | | | |
|---|---|---|---|---|
| DE | 2102011016311 A | | 10/2012 | |
| WO | 2003041782 A | | 5/2003 | |
| WO | WO 03/041782 | * | 5/2003 | ............ A61M 25/00 |
| WO | 2009012492 A | | 1/2009 | |
| WO | 2010149168 A | | 12/2010 | |

* cited by examiner

*Primary Examiner* — Bhisma Mehta
*Assistant Examiner* — Brandy S Lee
(74) *Attorney, Agent, or Firm* — Andrew Wilford

(57) ABSTRACT

The invention relates to a blood cannula for discharging blood into a vessel, in particular aortic cannula for discharging blood into an aortic arch during heart-bypass surgery, comprising a tubular body (1), the tubular body having a straight part at the proximal end (2) and a bent part at the distal end (3) leading into an outlet opening (5), wherein the distal end (3), in particular the bent part has an increasing cross section in the direction of blood flow (B).

11 Claims, 4 Drawing Sheets

BLOOD CANNULA

CROSS REFERENCE TO RELATED APPLICATIONS

This application is the US-national stage of PCT application PCT/EP2014/000004 filed 6 Jan. 2014 and claiming the priority of European patent application 13000286.8 itself filed 21 Jan. 2013.

FIELD OF THE INVENTION

The invention relates to a blood cannula for discharging blood into a vessel, comprising a tubular body, the tubular body having a straight part at the proximal end and a bent part at the distal end leading into an outlet opening.

BACKGROUND OF THE INVENTION

Such a cannula is known in the state of the art and is typically used for discharging oxygenized and/or cleaned blood into the aortic arch during heart-bypass surgery or during the use of an heart-lung-machine. Accordingly such a cannula is often named as aortic cannula. The application of a blood cannula is not restricted to field and accordingly the cannula can be used for any vessel.

The proximal end with the straight part of the tubular body has an inlet opening into which the blood is delivered from a pump, in particular a pump of a heart-lung-machine. The inlet opening may communicate with a hose connector. The blood passes through the straight part which provides a straight mean direction of flow. This straight mean direction corresponds to the geometrical middle axis of the straight part of the tubular body. The straight part leads into a bent part of the tubular body at its distal end thus redirecting the mean blood flow direction into a curved flow path, in particular essentially also corresponding to the geometric middle line of the bent part. This bent part leads into the outlet opening of the cannula.

The bent part of the tubular body assist insertion of the cannula into a vessel, particularly in curved vessels like the aortic arch.

On the outer surface of the tubular body a flange part which surrounds the tubular body may be positioned in the transition area between straight part and bent part. This flange part may help to position and/or fix the cannula with respect to the vessel and may also help to seal the punctured vessel.

Typical cannulas of the common kind provide a constant cross section of the distal part or even a tapered cross section in flow direction. Even though this helps insertion of the cannula into a vessel the disadvantage is that the blood is accelerated prior to exit. In combination with the surrounding vessel after insertion a venturi-effect may be observed which causes problems since it constricts the blood flow into smaller vessels branching off the aortic arch.

OBJECT OF THE INVENTION

It is an object of the invention to provide an improved cannula that helps to decelerate the blood in the distal end and particularly that helps to improve blood entry also into smaller vessels that branch off the aortic arch like vessels leading to head and brain.

SUMMARY OF THE INVENTION

According to the invention this object is achieved by means of a cannula having a bent part with an increasing cross section in the direction of blood flow. Bending may be extended over an angle of 90° or less particularly within a specific plane.

Due to the increasing cross section of the bent part upstream of the outlet opening the velocity of the blood is reduced and thus a venturi-effect avoided or at least significantly reduced. Accordingly the inventive cannula helps to distribute the discharged blood into the aortic arch and into vessels branching off the arch.

A simple embodiment may provide that the bent part has the form of a bent funnel having circular cross section or a cross section deviating from circular form.

At least the geometrically expanding bent part of the tubular body may be made of a collapsible material or elastic material, for example silicone. By collapsing the bent part or urging the bent part into a smaller form by external forces the insertion of the distal end of the tubular body into the vessel is facilitated. After the insertion the bent part gets back to his original, geometrically expanding form and provides the inventive advantages as described.

In order to minimized the puncture of the vessel the tubular body may be tapered in the flow direction in the straight part until the transition into the bent part having expanding/increasing cross section in flow direction. This provides a smallest cross section or diameter of the cannula in the area of transition between straight part and bent part, in particular in an area where the flange is positioned on the outer surface of the tubular body. After insertion into a vessel this smallest area may be positioned in the punctured vessel wall.

If not specifically mentioned any features regarding a cross section in this embodiment or later described embodiments may be understood in a way that the cross section is measured perpendicular to the mean direction of flow or perpendicular to the geometrical middle line/axis of the tubular body at the respective position.

In order to provide an increasing cross section of the distal end, in particular the bent part the cross section may be circular with increasing diameter in the flow direction. This embodiment may be understood as the simplest possible kind.

Simulative evaluation of such a form has shown that the flow of blood in the interior of the bent part is concentrated in the area of bigger radii compared to the area of smaller radii, the respective radius being measured starting from the point around which the bent part is bent. This leads to a non-uniform velocity distribution over the cross section of the bent part, in particular a bent part having circular cross section.

Accordingly an improvement of the invention may provide a distal end or bent part having an angle of expansion which is non-constant in the direction of the circumference of the increasing distal end. In particular such an angle of expansion may be defined as the angular difference between the tangent of a distal end deemed to have constant cross section and the tangent of the increasing distal end. Preferably the angle of expansion may be limited to 20° or less.

A preferred embodiment may provide a distal end or bent part having a cross section of the outlet opening, in particular also a cross section of the bent part upstream of the outlet opening which is not circular. This may help homogenize the velocity distribution of the blood over the cross section. Preferred form of the cross section may be elliptical or formed as a closed loop with a concave part in the loop, particularly formed as a generally elliptical loop with a concave part in the loop or formed as a generally circular loop with a concave part in the loop or formed like a kidney or formed like a sickle or formed like half-moon.

Particularly the cross section may be measured in the plane of the outlet opening or perpendicular to the mean direction of blood flow or perpendicular to the middle line/axis of the tubular body at the respective position.

In case of an elliptical cross section the smaller axis of the ellipse may be positioned in the plane of bending the bent part or tilted out of this plane by less than 45°.

In case of cross sections having a concave part in the closed circumferential loop of the cross section this concave part may be preferably positioned nonsymmetrical with respect to the plane in which the bent part is bent, in particular meaning that this plane intersect the cross section asymmetrically thus leading to two different shaped halves of the cross section. Preferably the above-described tilted form of the cross section or the asymmetrically intersected form may be used in connection with the following improvement.

An improvement may provide that at least in the straight part of the tubular body at least one wall is provided on the inner surface of the tubular body which is helically extending in the direction of blood flow. This will cause a blood flow on a helical path within the straight part and accordingly a rotation of the blood around the mean flow direction. Such a rotation will also extent into the bent part and into the vessel and will help to distribute the blood into vessels branching off the aortic arch.

The height of the at least one wall, in particular measured between the inner surface of the tubular body and the apex of the wall, may be at least partially increasing in the direction of blood flow, preferably in the beginning, (regarding in direction of flow). Particularly in the beginning of the wall the height may be zero.

Particularly for the case that the straight part of the tubular body is tapered as described before the at least one wall may have an area of decreasing height in the direction of blood flow, thus providing an area of extension in the direction of blood flow in which the distance between the apex of the wall and the mean axis of blood flow or the geometrical middle axis in this tapered straight part of the tubular body is constant.

In such a case but also in general for any other embodiments having at least one helical wall the height of the at least one wall may be chosen such that an unobstructed direct linear way exists for the blood within the straight part of the tubular body that is collinear preferably coaxial with the mentioned mean axis of blood flow or the geometrical middle axis of the straight part. Preferably such an unobstructed way may be kept small, in particular smaller than 25% or preferably smaller than 10% of the cross section of the straight part at its smallest position.

Another improvement may provide that in the direction of mean blood flow at least an end part of the at least one helically wound wall has a height between the inner surface of the straight part and the apex of the wall such that no unobstructed direct linear way exists for the blood within the straight part of the tubular body, in particular meaning that the height of the wall in this area is bigger than the distance between the inner wall and the axis of mean blood flow/ geometrical middle axis in the straight part. As a consequence no more linear flow of blood exist and all the blood is rotated.

A further improvement that may be combined with any of the above-described embodiments may provide at least one opening being positioned in the bent part of the tubular body and preferably being aligned with or intersected by the mean direction of blood flow in the straight part of the tubular body. Such an opening may be symmetrically intersected by the plane in which the bent part is bent. The opening may be circular or elliptical or of any other form.

BRIEF DESCRIPTION OF THE DRAWING

In the following different embodiments of the invention will be explained in more detail, with reference to the drawing in which.

SPECIFIC DESCRIPTION OF THE INVENTION

Figure 1:
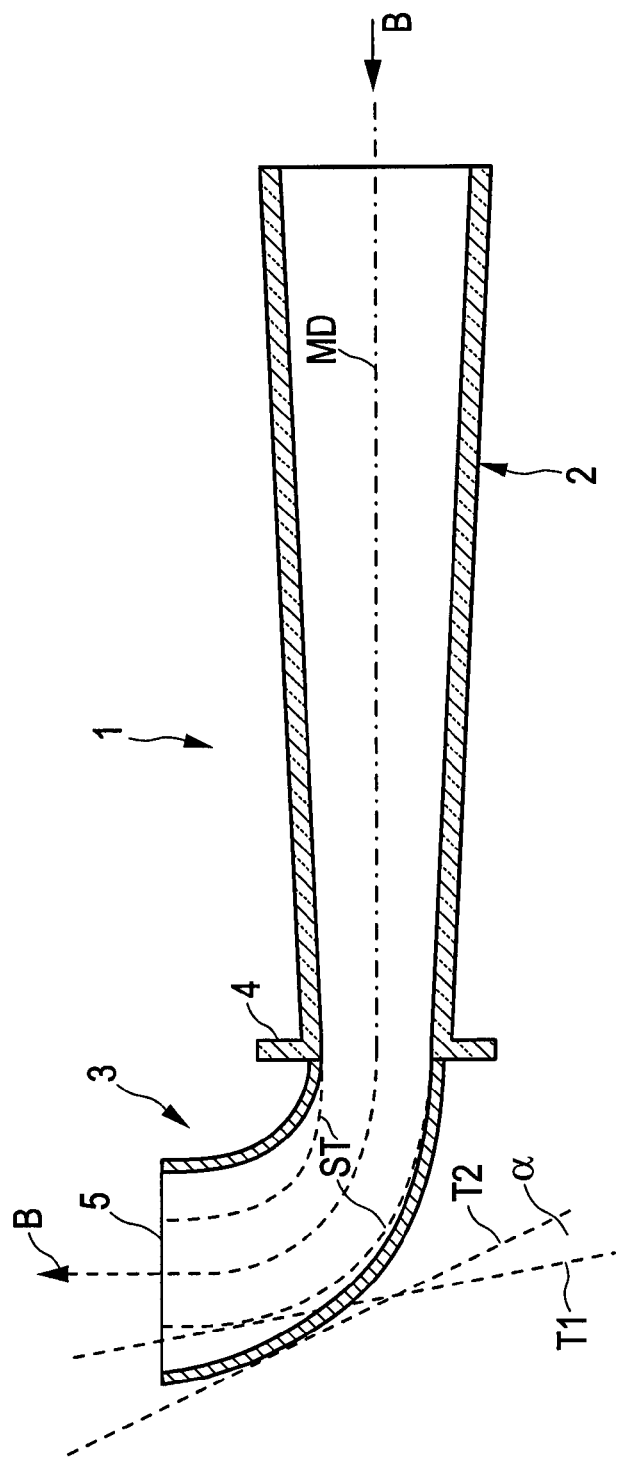
FIG. 1 is a vertical and longitudinal section through the cannula of this invention.

FIG. 1 shows a sectional view of a cannula according to a first embodiment in the plane of the bending of the cannula, which corresponds to the plane of the paper-sheet. The cannula comprises a tubular body 1 having a proximal end 2 and a distal end 3. The proximal end 2 has a straight form and is tapered from the beginning in the direction of the blood flow, indicated by the arrow B. The cross section of the distal end 3 is extending in the direction of flow, the expansion starting from the point where a flange 4 surrounds the tubular body at its internal waist. The mean direction of the blood flow is indicated by a dashed line MD, essentially corresponding to the geometrical middle line of the tubular body 1.

In order to visualize the difference between invention and state of the art there is furthermore indicated by dashed line ST the form of a conventional cannula having a constant cross section beyond the flange.

As can be seen the expansion is here given by the fact that an expansion angle $\alpha$ exists, measured between a tangent T1 on the conventional cross section and a tangent T2 on the inventive cross section. This angle is preferably smaller than 20° and can be, but need not to be constant an all circumferential points of a given cross section.

According to the expansion of the distal end 3 the blood velocity is reduced on the outlet opening 5 in comparison to the state of the art.

The cross section of the of the distal end 3 measured perpendicular to the mean direction of blood flow MD or measured in the plane of the outlet opening 5, which may also be perpendicular to this direction can be circular in a first simplified embodiment.

Figure 2:
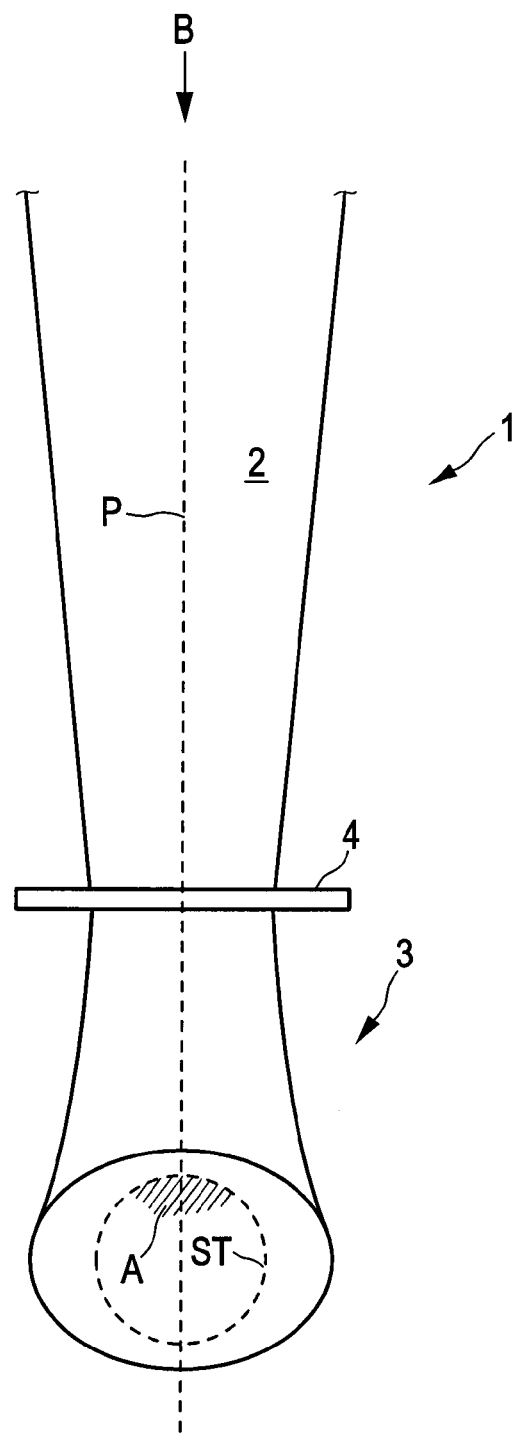
FIG. 2 is a partial top view of the cannula of FIG. 1.

According to a first improvement shown in FIG. 2 the cross section may by deviating from a circular form and may be elliptical having the smaller axis of the ellipse in the plane P of bending which is perpendicular to the paper sheet in FIG. 2 or—not shown—slightly tilted by not more than 45°.

The difference between the invention and the state of the art is shown by the dashed line ST, indication a conventional cannula. Such a form provides a more even velocity distribution of the blood over the cross section compared to the circular state of the art that suffers from a lower blood velocity in the inner part of the bent distal end which is indicated by the dashed area A.

Figure 3:
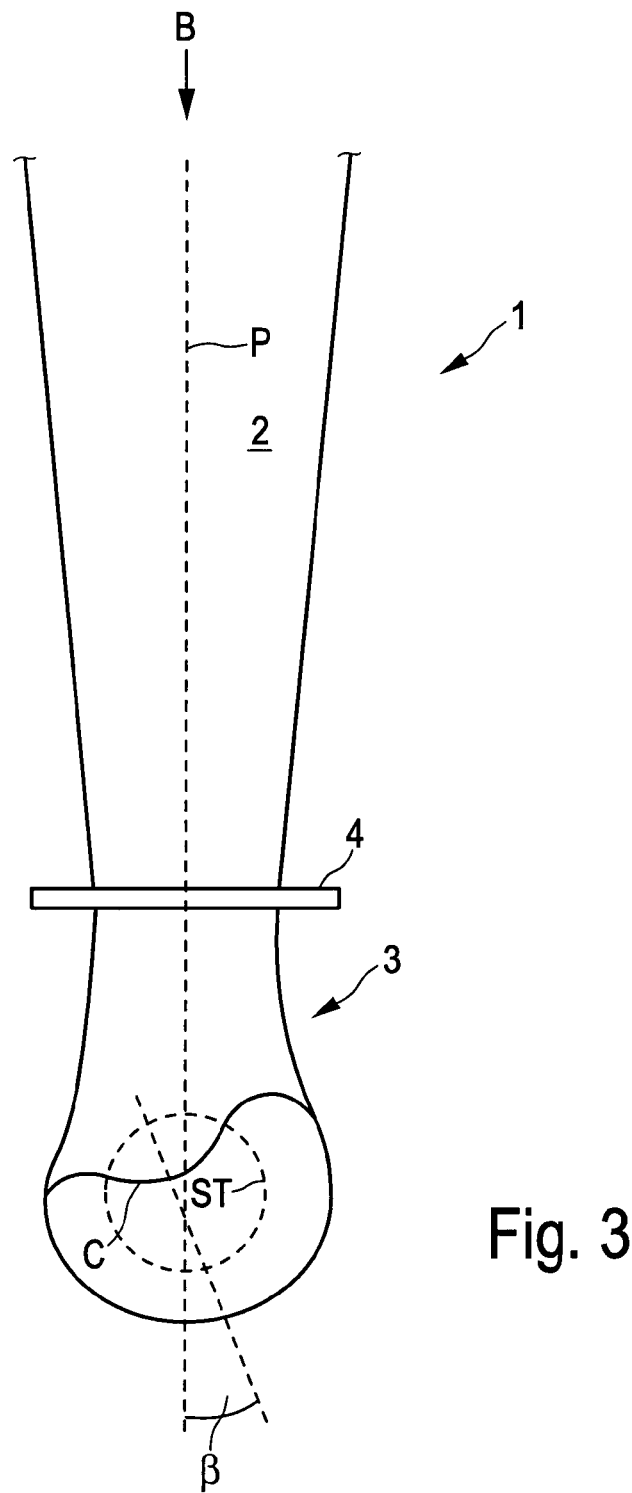
FIG. 3 is a view like FIG. 2 of a variant of the invention.

Another inventive improvement is shown in FIG. 3. Here the cross section form a closed circumferential loop having a partial concave area C. This concave area C may be positioned where the state of the art suffers from reduced blood velocity and possible turbulence. Accordingly the position may be such that the cross section is symmetrically intersected by the bending plane P (perpendicular to the paper-sheet) into two identical halves. This embodiment is not shown.

In particular when a helical flow of the blood is provided the area of reduced blood velocity is moved out of this plane and accordingly the area C of concave loop may be tilted in the same direction by an angle β thus providing a more even velocity distribution over the cross section and less turbulence compared to the state of the art.

The circumferential loop of an inventive cross section in the distal end may also be described by the fact that the angle of expansion α as shown in FIG. 1 shows two sign changes when regarded as a function of circumferential position. These changes are at the positions where the cross section of the invention is intersected by the cross section of the state of the art.

The cross section shown in FIG. 3 may be described as kidney-shaped, half-moon and is in this case a concave deviation from a circular form.

Figure 4:
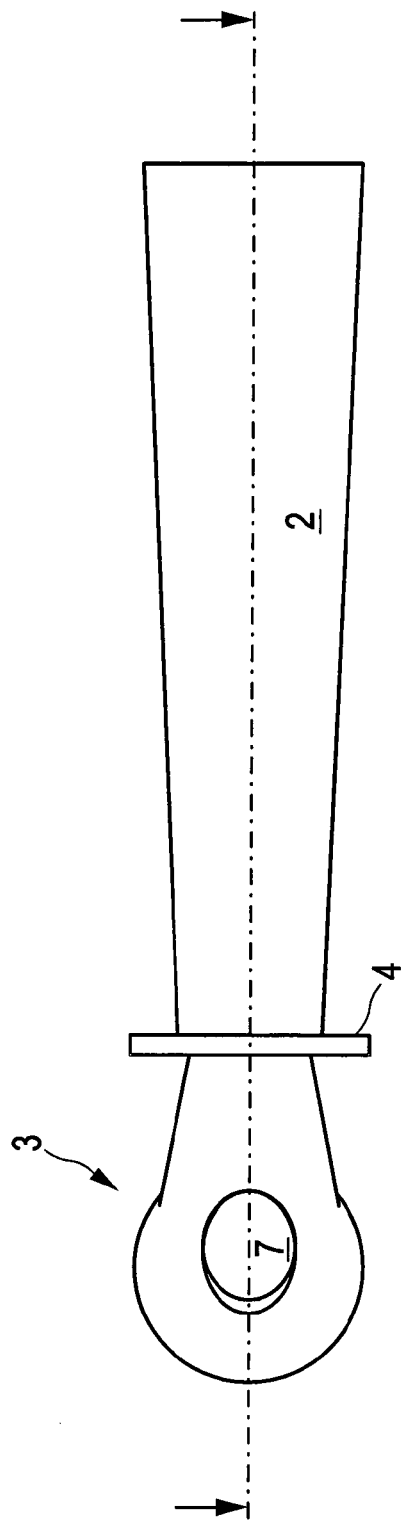
FIG. 4 is a bottom view and a longitudinal sectional view of another embodiment of the invention.
Figure 4:
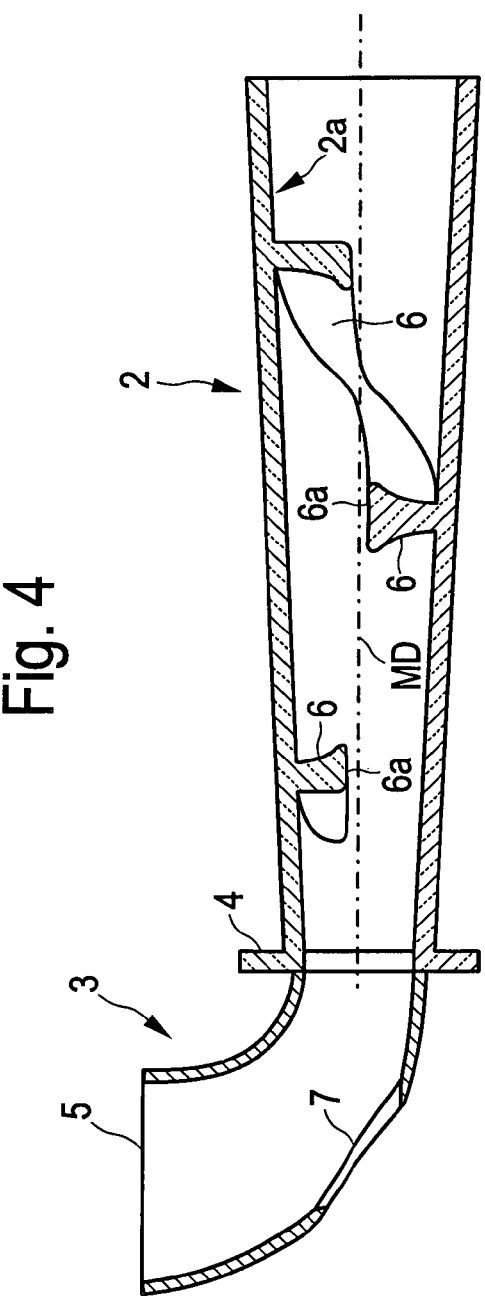

FIG. 4 shows another improvement that may be combined with any other embodiment, in particular the ones of the previous figures.

As can be seen a helically wound wall 6 is positioned on the inner surface 2a of the tapering proximal end 2. Such a helical wall 6 urges the blood to rotate around the mean direction of flow MD or geometric middle of the tubular body. The rotation extends into the bent distal end and also into the exterior of the cannula beyond the outlet 5. In this embodiment the apex 6a of the wall 6 has a distance to the mean direction of flow or geometric middle. Such a distance may be also omitted, i.e. zero or negative in a specific embodiment.

The helical wall may be combined with at least one additional opening 7 in the distal end, but such an opening 7 is not mandatory for the embodiments. The opening 7 may be positioned such that it is intersected by the mean direction of flow in the tapered straight part 2.

The invention claimed is:

1. A blood cannula for discharging blood into a vessel during heart-bypass surgery, the cannula comprising:
    a tubular body having a straight part at a proximal end and a bent part at a distal end leading into an outlet opening, the bent part having an increasing cross section in a direction of blood flow through the cannula; and
    a helical wall extending in the direction of blood flow on an inner surface of the straight part, a height of the helical wall measured between an inner surface of the tubular body and an apex of the wall increasing in the direction of blood flow in a beginning of its extension starting with a height of zero, the wall having an area of decreasing height in the direction of blood flow so as to form an area of extension in the direction of blood flow in which a spacing between the apex of the wall and a geometric center of the straight part in the straight part of the tubular body is constant.

2. The blood cannula according to claim 1, wherein an angle of expansion of the distal end is non-constant in a direction of a circumference of the distal end, the angle of expansion being an angular difference between a tangent of a distal end having a constant cross section and the tangent of the distal end.

3. The blood cannula according to claim 2, wherein the angle of expansion is less than 20°.

4. The blood cannula according to claim 1, wherein the straight part is tapered in the direction of blood flow and has a region of smallest cross section in an area of transition between the straight part and the bent part.

5. The blood cannula according to claim 1, wherein a cross section of the outlet opening and of the bent part upstream of the outlet opening is not circular and is:
    a) elliptical, or
    b) formed as a closed elliptical loop with a concave part in the loop or as a generally circular loop with a concave part in the loop, or
    c) formed like a kidney, or
    d) formed like a sickle, or
    e) formed like half-moon, the cross section of the outlet opening lying in a plane of the outlet opening or perpendicular to the direction of blood flow.

6. The blood cannula according to claim 5, wherein the concave part of the closed loop of the cross section is asymmetric with respect to a plane in which the bent part is bent.

7. The blood cannula according to claim 1, wherein at least the bent part of the tubular body is made of an elastic and/or collapsible material.

8. The blood cannula according to claim 1, wherein a height of the helical wall is such that an unobstructed direct linear path exists for blood flowing in the direction within the straight part of the tubular body, the straight path being collinear and coaxial with the direction of blood flow or a geometrical centerline of the straight part.

9. The blood cannula according to claim 8, wherein the opening is symmetrically intersected by a plane in which the bent part is bent.

10. The blood cannula according to claim 1, wherein in the direction of mean blood flow, at least an end part of the helical wall has a height between the inner surface of the straight part and the apex of the wall such that no unobstructed direct linear way exists for the blood within the straight part of the tubular body and a height of the wall in this area is greater than a spacing between the inner surface and a geometric center of the straight part.

11. The blood cannula according to claim 1, wherein at least one opening is formed in the bent part of the tubular body aligned with or intersected by the direction of blood flow in the straight part of the tubular body.

* * * * *